(12) United States Patent
Hanson

(10) Patent No.: US 10,300,242 B2
(45) Date of Patent: *May 28, 2019

(54) SLEEP TRAINING CHILD NIGHT LIGHT

(71) Applicant: Hush Buddy, LLC, Raleigh, NC (US)

(72) Inventor: Scott Hanson, Raleigh, NC (US)

(73) Assignee: Hush Buddy, LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,112

(22) Filed: Feb. 13, 2018

(65) Prior Publication Data

US 2018/0169374 A1    Jun. 21, 2018

Related U.S. Application Data

(63) Continuation-in-part of application No. 15/341,197, filed on Nov. 2, 2016, now Pat. No. 9,930,755.

(51) Int. Cl.
*A61M 21/02* (2006.01)
*A61M 21/00* (2006.01)
*F21V 23/04* (2006.01)

(52) U.S. Cl.
CPC ..... *A61M 21/02* (2013.01); *A61M 2021/0044* (2013.01); *A61M 2205/3375* (2013.01); *A61M 2230/63* (2013.01); *F21V 23/0442* (2013.01)

(58) Field of Classification Search
CPC .......................... H05B 37/02; H05B 37/0236; H05B 37/0281; H05B 37/0272; H05B 37/0227; A61M 21/00; A61M 21/02; A61M 2230/63; A61M 2021/0027; A61M 2021/0083; G08B 5/36; G08B 21/02; G08B 21/0202; F21V 33/00; F21V 23/0442; G01L 25/78

See application file for complete search history.

(56) References Cited

U.S. PATENT DOCUMENTS

| | | | | |
|---|---|---|---|---|
| 3,898,383 | A | * | 8/1975 | Herbits ................. H02M 1/096 315/291 |
| 5,307,051 | A | | 4/1994 | Sedlmayr |
| 6,020,659 | A | | 2/2000 | Crowther et al. |
| 6,822,556 | B2 | * | 11/2004 | Burns ..................... G08B 5/36 340/321 |
| 8,398,538 | B2 | | 3/2013 | Dothie et al. |
| 9,530,080 | B2 | | 12/2016 | Glazer |
| 9,681,519 | B2 | * | 6/2017 | Smith ............... H05B 37/0218 |
| 9,930,755 | B1 | * | 3/2018 | Hanson .................... G09B 5/00 |
| 2004/0257814 | A1 | | 12/2004 | Eusterbrock |
| 2007/0279234 | A1 | * | 12/2007 | Walsh ................... A61M 21/00 340/573.1 |
| 2008/0204258 | A1 | * | 8/2008 | Dayton .............. F21V 23/0442 340/600 |
| 2017/0258398 | A1 | * | 9/2017 | Jackson .............. A61B 5/4812 |

* cited by examiner

*Primary Examiner* — Haissa Philogene
(74) *Attorney, Agent, or Firm* — James G. Passé; Passé Intellectual Property, LLC

(57) ABSTRACT

The present invention relates to a device and method of training a child to go to sleep by providing a light which dims in response to a child sound or a presence other than the child and turns back on or brightens when the sound stops or the presence leaves.

10 Claims, 4 Drawing Sheets

SLEEP TRAINING CHILD NIGHT LIGHT

This application is a continuation-in-part of U.S. non-provisional application Ser. No. 15/341,197 filed on Nov. 2, 2016, and which is incorporated herein in its entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a device for sleep training children. In particular, it relates to a night light which dims when a child makes noise or someone enters a child's room and brightens when they don't make noise, to encourage children who like night lights to go to sleep.

Description of Related Art

The use of a night light in a child's room is very common. While some children can have the light extinguished after they go to sleep, many, if not most, require the light to be on all night long. The child feels it is comforting and creates a safe space for them to sleep in without adults or guardians in the room.

Children, early on, cry for food or to be changed, but as they get older, crying, talking, and staying up at night are just for attention and frequently require someone to check on the child to help the child. This encourages continued crying, talking, and staying awake and gets very difficult for the adult who needs to get up at night during the process. Many methods are used to stop a child from crying and making noise, including letting them cry and just plain waiting till they stop as they get older. For some, this is neither practical nor effective. New methods for stopping children from crying and talking and encouraging them to go to sleep during the night are desperately needed.

BRIEF SUMMARY OF THE INVENTION

The present invention is the discovery of a method and device for training children to stop crying or making noise and going to sleep, especially those that also utilize a night light. In the present invention, a child's night light is fitted with a dimming circuit that engages if it senses a child making noise or someone enters the room, the light dims, but if the child remains quiet or the person leaves, the light remains on or brightens if it had previously dimmed. Since the child will want the night light on, the child learns if they don't make noise or call out to a parent, the night light stays on.

Accordingly, in one embodiment, there is a night light system for use in sleep training a child who sleeps with the night light on comprising:
a) a light dimming circuit;
b) a sensor designed to detect at least one of the sound of the child and the presence of someone in addition to the child or the child leaving the room or getting up; and
c) a connecting circuit for using the dimming circuit to dim the light when the sensor detects the childsound or presence of someone and turning the light up after a period of time when no child sound or presence is sensed by the sensor.

In yet another embodiment, there is a method of training a child to be quiet and go to sleep at night while using a night light, the method comprising:
a) engaging a sensor that detects at least one of when the child is making a sound or there is a presence of someone other than the child;
b) when the sensor detects the child sound or the presence, sending a signal to a dimming circuit on the night light which instructs the dimming circuit to lower the light intensity; and
c) engaging a timer to time how long it has been since the sound was detected lastor the presence has left and increasing the light intensity once a selected time is reached.

DETAILED DESCRIPTION OF THE INVENTION

Figure 1:
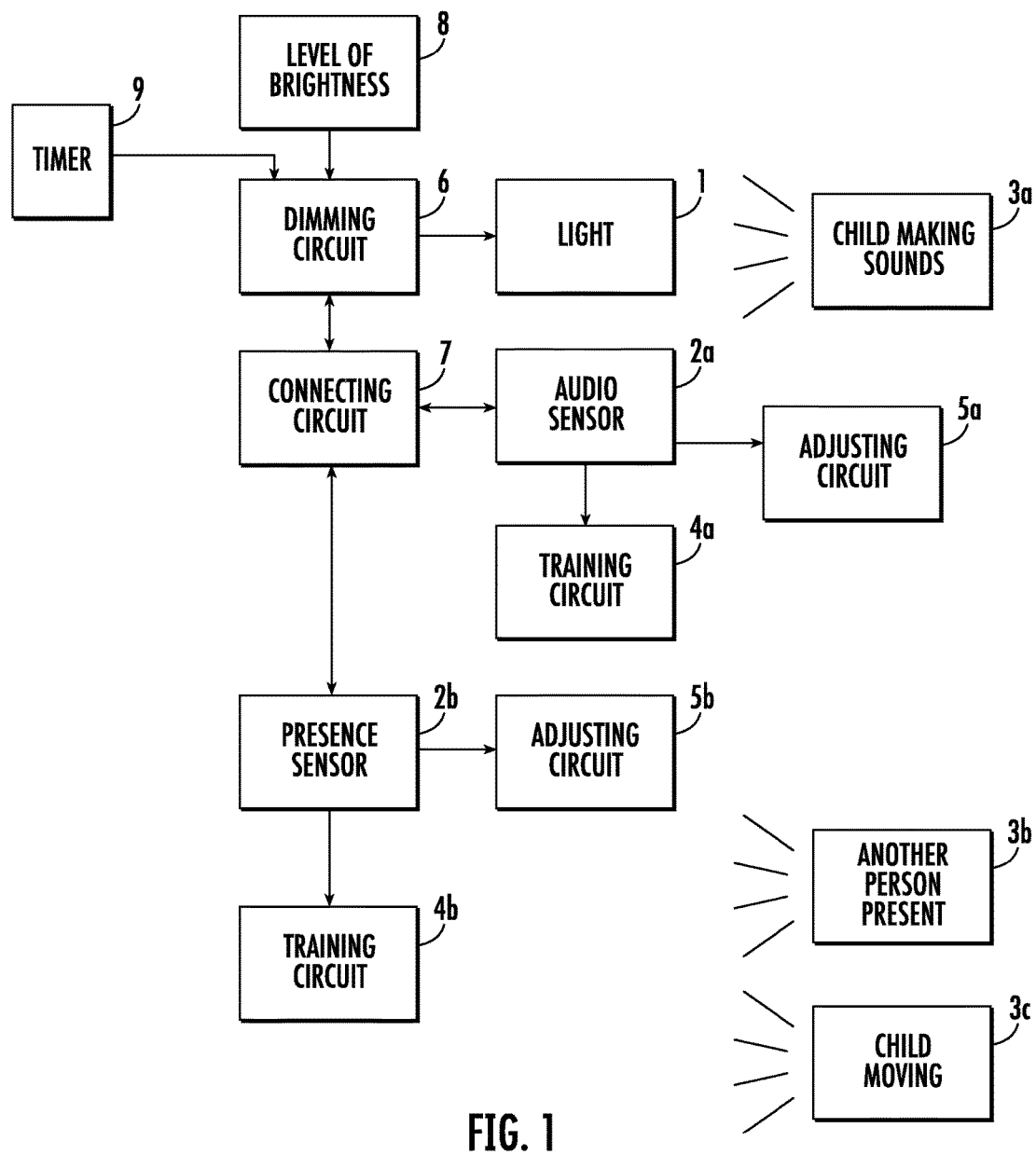
FIG. 1 is a diagram of the present invention.

While this invention is susceptible to embodiment in many different forms, there is shown in the drawings, and will herein be described in detail, specific embodiments with the understanding that the present disclosure of such embodiments is to be considered as an example of the principles and not intended to limit the invention to the specific embodiments shown and described. In the description below, like reference numerals are used to describe the same, similar, or corresponding parts in the several views of the drawings. This detailed description defines the meaning of the terms used herein and specifically describes embodiments in order for those skilled in the art to practice the invention.

Definitions

The terms "about" and "essentially" mean ±10 percent.
The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.
The term "comprising" is not intended to limit inventions to only claiming the present invention with such comprising language. Any invention using the term comprising could be separated into one or more claims using "consisting" or "consisting of" claim language and is so intended.
References throughout this document to "one embodiment", "certain embodiments", "an embodiment," or similar terms means that a particular feature, structure, or characteristic described in connection with the embodiment is included in at least one embodiment of the present invention.

Thus, the appearances of such phrases in various places throughout this specification are not necessarily all referring to the same embodiment. Furthermore, the particular features, structures, or characteristics may be combined in any suitable manner in one or more embodiments without limitation.

The term "or," as used herein, is to be interpreted as an inclusive or meaning any one or any combination. Therefore, "A, B, or C" means any of the following: "A; B; C; A and B; A and C; B and C; A, B, and C". An exception to this definition will occur only when a combination of elements, functions, steps, or acts are in some way inherently mutually exclusive.

The drawings featured in the figures are for the purpose of illustrating certain convenient embodiments of the present invention, and are not to be considered as limitation thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "child" refers to a baby or young child in a room at night in the process of going to sleep with a night light. The child is one that still cries, makes noise, or requires an adult to come to the room at night but is old enough to be trained about making noise or call for a parent. The minimum age will vary from child to child, but in one embodiment, the child is at least 3 months old. In another embodiment, the child is about 2-4 years old.

As used herein, the term "presence of someone" refers to a person, such as a parent or other adult, the child or other than the child that comes to or leaves (such as the child leaving the room) where the child is trying to go to sleep, e.g. in the child's room. By detecting the presence or absence of a person, the dimming of the light will discourage the child from calling for a parent, leaving the bed, or the like and concentrate on going to sleep.

As used herein, the term "light" refers to a battery or electric operated light in a child's room designed to be kept on while the child sleeps. A night light that plugs into the wall, a lamp, or a ceiling light are all included depending on what a child uses in their room as a night light. The light can be, in one embodiment, controllable using a computer, smartphone, or the like. In one embodiment, the light can be controlled by a digital assistant with a microphone (e.g. Alexa or Google Home) which can control the light.

As used herein, the term "child sound" refers to a child weeping, shedding tears, talking, making noises, or the like. Because a child's sound is very pitch definite, it is possible, in one embodiment, to use a sensor that is only tuned to those higher frequencies associated with a child's sounds. In one embodiment, the child sound is any sound above a certain decibel. In another embodiment, the sensor is tuned to a sound frequency of the child. In general, any noise the child makes could constitute a sound therefore, for example, if the child is playing with a toy late at night and making sounds, this could be considered a sound.

As used herein, the term "dimming circuit" refers to an AC or DC circuit which reduces electrical current to a light and thus reduces the light output of the light. It can be a simple on/off switch, a rheostat type dimming, a digital assistant controlled dimming, or some form of step dimming, so that multiple steps occur before the light is all the way off. It also refers to being able to reverse the dimming process, thus brightening the light in the same or similar manner to the dimming of the light, the brightening could be controlled by a timer (e.g. so many minutes or seconds after sound stops or any other method). While the circuits of the present invention could be separate chips, devices, or the like, in one embodiment, the circuits are all on one chip and, in a further embodiment, the chip is connected to the light where a digital assistant is utilized, the assistant would send a signal to a dimming circuit controlling the light (e.g. Lutron).

As used herein, the term "connecting circuit" refers to an electronic circuit (wired or wireless) that coordinates information from an audio sensor and the dimming switch. It lets the dimming circuit know that the audio sensor has or has not received information that would cause the dimming circuit to operate, either dimming or brightening the light.

As used herein, the term "sensor" refers to one of first an audio sensor, a circuit that detects sound near the child, a presence sensor detecting the presence or lack of presence of someone, and the like. In one embodiment, it is any sound over a certain decibel level detected by the sound sensor. In other embodiments, it is tuned to pitch, the length of the sound, or the time there has been no sound. In one embodiment, it is designed to be tuned to an individual child's sounds, or frequency of sound, or the like, thus ignoring any sound which is not the child's. A presence sensor detects the presence of another person in the room with the child, the child getting up and leaving the room or the bed, e.g. by use of Bluetooth in a smartphone. In one embodiment, the sensor is in a digital assistant.

DRAWINGS

Now referring to the drawings, FIG. 1 is a diagram of thenight light system of the present invention connected to light 1. It could be a free standing light, light on a smart phone, light controlled by a digital assistant, or the like. An audio sensor 2a or presence sensor 2b is positioned where it can detect either a child sound 3a or a presence sensor 3b for detecting someone in child's room or the child moving 3c. The audio sensor 2a can have an optional training circuit 4a where it learns the child's voice or general sound and/or can have an adjustment circuit 5a which allows the sensor to detect based on sound intensity, frequency, type and/or duration of the sound, and the like, detected before engaging the dimming circuit 6 using the connecting circuit 7. Likewise, the presence sensor 2b can have a training circuit 4b where it learns how/who to detect and can save an adjustment circuit 5b from adjusting distance, individuals, and the like before engaging the dimming circuit 7. The dimming circuit 6 can keep track of levels of brightness 8 in steps in a continuous manner or simply an on/off manner. Controlling the light intensity up or down as determined by whether it is detecting sound, and dimming the light down when detecting a sound or, if no sound has been detected in the timeframe, turning the light up. A timer 9 is shown for timing when the light will re-brighten. There can also be additional lighting patterns for other detection by the device.

Figure 2:
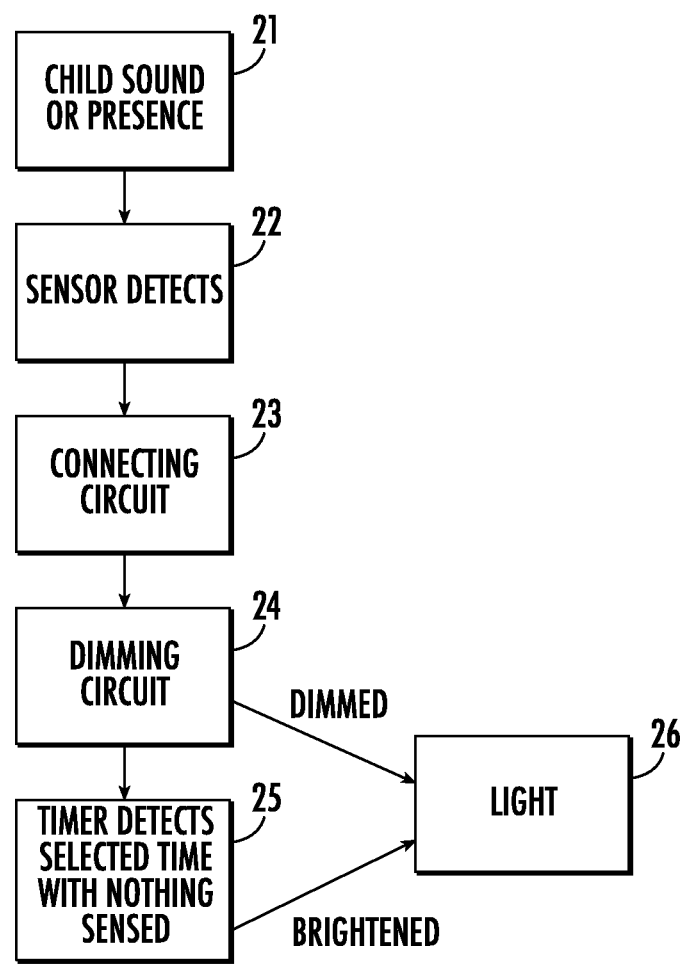
FIG. 2 is a flowchart of the method of the present invention.

FIG. 2 depicts the method of the present invention for teaching a child to go to sleep at night while using a night light. In the present method, when a child makes a sound or there is a presence 21, a sensor detects 22 the sound or presence. A connecting circuit 23 then transfers detected information to the dimming circuit 24 which then dims light 26. A timer 25 is engaged with a time selected for a time period with nothing detected, and after that time period is achieved, the light 26 is brightened back up either in steps or all at once.

Figure 3:
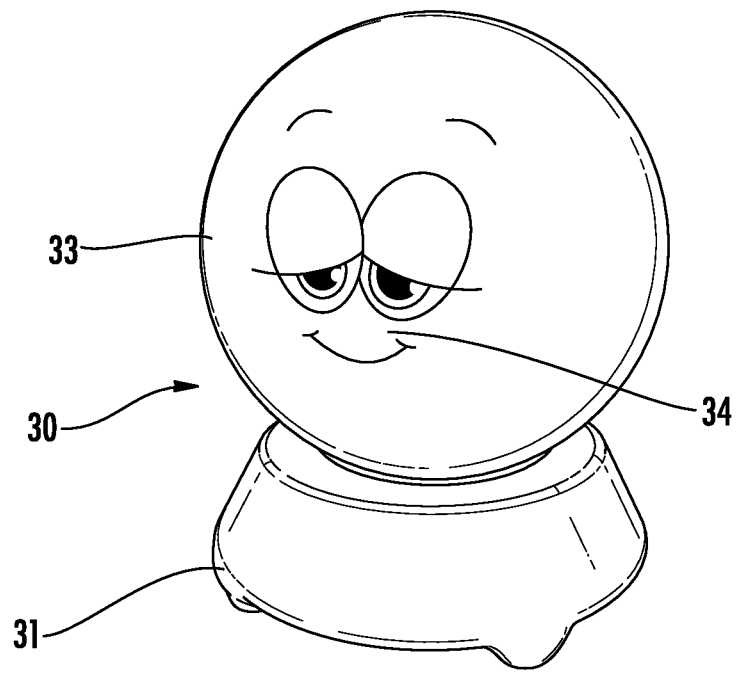
FIG. 3 is a front view of an embodiment of the device.

FIG. 3 is an embodiment of the night light system that is self-contained in one unit. In this view, night light system 30 comprises a base 31 which contains light dimming circuit sensor and connecting circuit. A light is contained in night light globe 33 and is controlled by the system. In this view, a pleasant face 34 is placed on the globe to help children be comfortable with the device.

Figure 4:
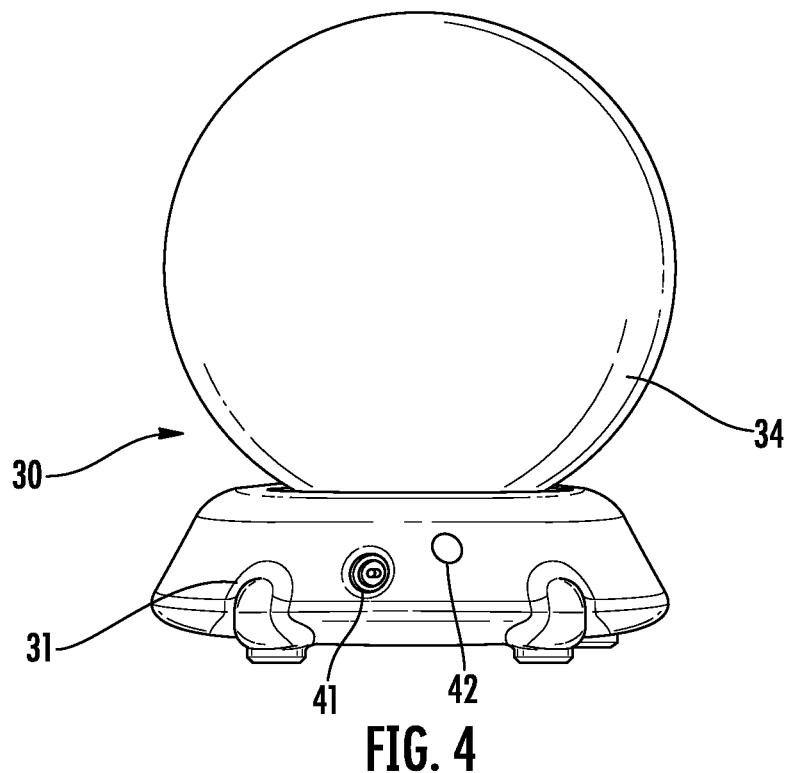
FIG. 4 is a back view of an embodiment of the device.
Figure 5:
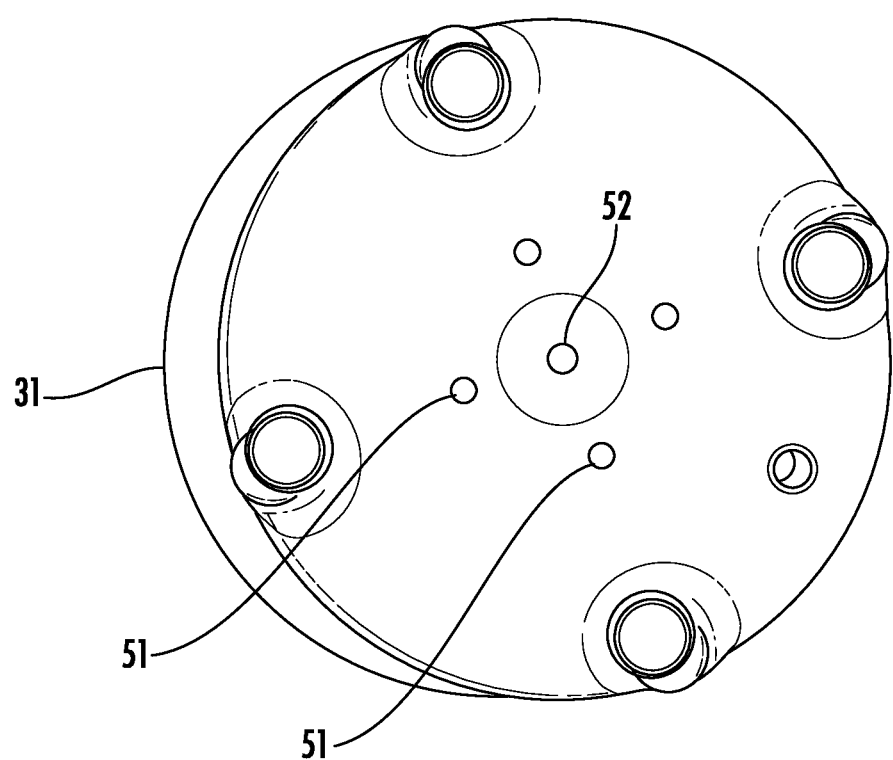
FIG. 5 is a bottom view of an embodiment of the device.

FIG. 4 is a back view of night light system 30 showing a power cord attachment 41 and a control switch 42. FIG. 5 is a bottom view of base 31 wherein there is a button 52 for setting the timer for how much time before the device returns to full brightness. LED indicator lights 51 are to indicate the settings from button 52.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials, and the like apparent to those skilled in the art still fall within the scope of the invention as claimed by the applicant.

What is claimed is:

1. A night light system for use in sleep training a child who sleeps with a night light on comprising:
   a) a light dimming circuit;
   b) a sensor designed to detect at least one of a sound of the child and a presence of someone in addition to the child or the child leaving a room or getting up; and
   c) a connecting circuit for using the dimming circuit to dim the light when the sensor detects the child sound or presence of someone and turning the light up after a period of time when no child sound or presence is sensed by the sensor.

2. The light system according to claim 1 wherein the sensor is trained to detect a particular child's sound.

3. The light system according to claim 1 wherein the dimming circuit dims the light in steps, including turning the light off.

4. The light system according to claim 1 wherein the connecting circuit is adjustable for at least one of time, length of sound, and sound intensity.

5. The light system according to claim 1 wherein the sensor is a Bluetooth sensor that senses the presence or absence of someone.

6. The light system according to claim 1 wherein the sensor is a digital assistant.

7. A method of training a child to be quiet and to go to sleep at night while using a night light, the method comprising:
   a) engaging a sensor that detects at least one of when the child is making a sound or there is the presence of someone other than the child;
   b) when the sensor detects the child sound or the presence, sending a signal to a dimming circuit on the night light which instructs the dimming circuit to lower the light intensity; and
   c) engaging a timer to time how long it has been since the sound was detected last or the presence has left and increasing the light intensity once a selected time is reached.

8. The method according to claim 7 wherein the night light dims in stages until the light is off.

9. The method according to claim 7 wherein the light dims when someone other than the child is near the night light.

10. The method according to claim 7 wherein the sensor is a digital assistant which can instruct the dimming circuit.

* * * * *